(12) United States Patent
Sato et al.

(10) Patent No.: US 10,188,362 B2
(45) Date of Patent: Jan. 29, 2019

(54) X-RAY FLUOROSCOPY AND IMAGING APPARATUS

(71) Applicant: SHIMADZU CORPORATION, Kyoto-Shi, Kyoto (JP)

(72) Inventors: Shota Sato, Kyoto (JP); Takihito Sakai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/867,317

(22) Filed: Jan. 10, 2018

(65) Prior Publication Data

US 2018/0206809 A1    Jul. 26, 2018

(30) Foreign Application Priority Data

Jan. 20, 2017 (JP) .................... 2017-008410

(51) Int. Cl.
*A61B 6/00*    (2006.01)
*G01T 1/20*    (2006.01)
*G01T 1/208*   (2006.01)
*G06T 7/00*    (2017.01)
*G06T 7/11*    (2017.01)
(Continued)

(52) U.S. Cl.
CPC ............ *A61B 6/5235* (2013.01); *A61B 6/461* (2013.01); *A61B 6/469* (2013.01); *A61B 6/487* (2013.01); *A61B 6/503* (2013.01); *A61B 6/504* (2013.01); *A61B 6/5205* (2013.01); *G01T 1/208* (2013.01); *G01T 1/2018* (2013.01); *G06T 7/0012* (2013.01); *G06T 7/11* (2017.01); *G06T 7/20* (2013.01); *G06T 11/60* (2013.01);
(Continued)

(58) Field of Classification Search
CPC ....... A61B 6/5235; A61B 6/461; A61B 6/469; A61B 6/487; A61B 6/503; A61B 6/504; A61B 6/5205; G06T 7/11; G01T 1/2018; G01T 1/208
See application file for complete search history.

(56) References Cited

U.S. PATENT DOCUMENTS 7,826,884 B2 * 11/2010 Baumgart ............... A61B 6/463
                                                       378/62
2006/0058647 A1 *  3/2006 Strommer ................ A61B 5/06
                                                       600/434
(Continued)

FOREIGN PATENT DOCUMENTS

JP    2005-510288    4/2005
JP    2008-520320    6/2008
(Continued)

*Primary Examiner* — Christine S. Kim
(74) *Attorney, Agent, or Firm* — Andrew F. Young, Esq.; Lackenbach Siegel, LLP

(57) ABSTRACT

An X-ray fluoroscopic imaging apparatus includes: an image generation element that generates the fluoroscopic images of the subject; an image processing element that executes an image processing to superimpose a plurality of fluoroscopic images that the image generation element continuously generates, and generates and displays the image denoting the movement locus of the marker that denotes the location of a stent introduced inside a body of the subject; and a region-of-interest setting element that set up the region-of-interest includes the movement locus relative to the superimposed image, in which the fluoroscopic images are superimposed one another.

8 Claims, 6 Drawing Sheets

(51) Int. Cl.
*G06T 7/20* (2017.01)
*G06T 11/60* (2006.01)

(52) U.S. Cl.
CPC ............... *G06T 2207/10121* (2013.01); *G06T 2207/30048* (2013.01)

(56) References Cited

U.S. PATENT DOCUMENTS

| | | | | |
|---|---|---|---|---|
| 2010/0256510 | A1* | 10/2010 | Leiblein | A61B 6/12 600/509 |
| 2015/0139394 | A1* | 5/2015 | Kang | A61B 6/5211 378/62 |

FOREIGN PATENT DOCUMENTS

| | | |
|---|---|---|
| JP | 2010-131371 | 6/2010 |
| JP | 2013-215247 | 10/2013 |
| JP | 2015-165942 | 9/2015 |
| JP | 2016-019724 | 2/2016 |

\* cited by examiner

⇩ Generate a stent fixed image

Select a magnified display portion ⇨

X-RAY FLUOROSCOPY AND IMAGING APPARATUS

CROSS REFERENCE TO RELATED APPLICATIONS

This application relates to, and claims priority from JP Ser. No. JP2017-008410 filed Jan. 20, 2017, the entire contents of which are incorporated herein by reference.

FIGURE SELECTED FOR PUBLICATION

FIG. 1

BACKGROUND OF THE INVENTION

Field of the Invention

The present invention relates to an X-ray fluoroscopy and imaging apparatus (X-ray fluoroscopic imaging apparatus).

Description of the Related Art

Conventionally, an X-ray fluoroscopic imaging apparatus that displays the location of a device introduced inside a body of a subject is known. Such X-ray imaging apparatus is disclosed in Patent Document JP2013-215247 A1.

The Patent Document 2013-215247 A1 discloses the X-ray fluoroscopic imaging apparatus that comprises an X-ray tube, and an X-ray detector that detects the X-ray that is irradiated from the X-ray tube and transmits a subject; and takes a fluoroscopic image including the device introduced inside the body of the subject and displays the X-ray image on the display element. According to the X-ray fluoroscopic imaging apparatus disclosed in the Patent Document 2013-215247, such X-ray fluoroscopic imaging apparatus prompts a user to set up a region-of-interest in which an X-ray reflection object other than the device is subtracted from the image including the device that is displayed on the display element, and in addition, the user can set up manually the region-of-interest while confirming the image (real-time video) of the region including the device that is continuously imaged and continuously displayed on the display element. And according to the X-ray fluoroscopic imaging apparatus disclosed in the Patent Document 2013-215247, the device in the set-up region-of-interest is fixed-and-displayed.

However, according to the X-ray fluoroscopic imaging apparatus disclosed in the Patent Document 2013-215247, it may be too hard for the user to set up the adequate region-of-interest in the aspect in which the user must manually set up the region-of-interest while confirming the real-time video. For example, the user must recognize the location of the device while confirming the real-time video during the operation in which the device inserted into the blood vessel is moving largely due to heartbeat under a coronary intervention that is a medical treatment on a myocardial infarction or an angina. The region-of-interest set up by the user preferably includes an entire region in which the device moves and is as narrow as possible so that the detection accuracy of the device on the image processing can be improved when the device is fixed and displayed. Therefore, the user must recognize accurately the location of the device and set up the region-of-interest within an optimal range even during the operation demanding the precious works.

ASPECTS AND SUMMARY OF THE INVENTION

The present invention has been proposed in order to solve the aforementioned problems, an object of the present invention is to provide an X-ray fluoroscopic imaging apparatus that facilitates the user to enable setting up the region-of-interest within the optimal range even when the device introduced inside the body of the subject is moving around.

To achieve the above problem, according to one aspect of the present invention, an X-ray fluoroscopic imaging apparatus comprises: an image generation element that generates a fluoroscopic image based on a detection signal of a radiation that transmits a subject; a display element that enables to display the fluoroscopic image; an image processing element that executes an image processing to superimpose a plurality of fluoroscopic images that the image generation element continuously generates, and generates an image denoting a movement locus of a benchmark denoting a location of a device introduced inside a body of the subject and display such generated image on a display element; and a region-of-interest setting element that sets up the region-of-interest including the movement locus relative to a superimposed image of the fluoroscopic images.

The X-ray fluoroscopic imaging apparatus, according to one aspect of the present invention set forth above, comprises: the image processing element that executes the image processing to superimpose a plurality of fluoroscopic images that the image generation element continuously generates, and generates the image denoting a movement locus of a benchmark denoting a location of a device introduced inside a body of the subject and display such generated image on a display element; and a region-of-interest setting element that sets up the region-of-interest including the movement locus relative to a superimposed image of the fluoroscopic images. Accordingly, the user can set up the region-of-interest having a minimum range including the movement locus while confirming the movement locus of the benchmark denoting the location of a device that the display element displays. Consequently, even when the device introduced inside the body of the subject moves, the movement region is demonstrated to be easily recognizable for the user, so that the user can set up easily the region-of-interest within an optimal range.

The movement locus relative to the X-ray fluoroscopic imaging apparatus according to one aspect as described above is preferably the movement locus that moves due to the heartbeat of the subject. Now, when the location of the device must be recognizable accurately while the device inserted inside the blood vessel moves largely in accordance with the heartbeat, during such as the coronary intervention; the present invention is particularly effective that the movement range is demonstrated to be easily recognizable for the user, so that the user can set up easily the region-of-interest within an optimal range even when the device introduced inside the body of the subject moves.

In such case, preferably, the image processing element superimposes a number of said fluoroscopic images, of which the number is equivalent to at least one per heartbeat, and displays the movement locus. According to such aspect, at least one cycle of the movement locus of the device, of which movement are periodically repeated by the heartbeat, can be displayed, so that the movement range of the device can be recognized more accurately.

According to one aspect of the X-ray fluoroscopic imaging apparatus set forth above, it is preferable that the image processing element display the candidate for the region-ofinterest in a selectable manner based on the movement locus. According to such aspect, the user can facilitate the operation compared to the case in which the user sets up the region-of-interest by surrounding the region using the operation element and so forth while making sure the movement locus that the display element displays so that the region-of-interest includes the movement locus. Particularly, when the other device than the target device or the region of the subject similar to the benchmark of the device is in the fluoroscopic image, the operator can extremely facilitate the operation to set up the region-of-interest when a plurality of the targets that the user watches is present. As results, the operator can facilitate the operation to set up the region-of-interest.

According to one aspect of the X-ray fluoroscopic imaging apparatus set forth above, preferably, the image processing element enable to generate the device-fixed image that is processed to fix-display the location of the device based on the location data of the device in the region-of-interest that is set up based on the data of the movement locus that the image processing element displays on the display element. According to such aspect, the device-fixed image can be generated along with locating assuredly the location of the device in the region-of-interest, so that the detection accuracy of the device in the device-fixed image can be improved. As results, the device can be assuredly fix-displayed.

According to one aspect of the X-ray fluoroscopic imaging apparatus set forth above, it is preferable that the image processing element displays the movement locus on the display element based on the brightness value relative to the fluoroscopic image. According to such aspect, the difference relative to the fluoroscopic image between the device and the subject can be clear by using the material haying a low transmittance at least for a part of the device, so that the location of the benchmark of the device relative to the fluoroscopic image can be clearly displayed. As results, the user can easily make sure the location of the device relative to the fluoroscopic image.

According to one aspect of the X-ray fluoroscopic imaging apparatus set forth above, it is preferable that the X-ray imaging apparatus further comprises an input element by which the user can input an input to set up the region-of-interest, and the region-of-interest setting element sets up the region-of-interest based on the data that the input element inputs. According to such aspect, the user can set up the region-of-interest within the range that the user desires.

According to one aspect of the X-ray fluoroscopic imaging apparatus set forth above, it is preferable that the device is a stent that is introduced inside the blood vessel. According to such aspect, even when the stent as the device introduced inside the body of the subject moves, the movement range of the stent is demonstrated to be easily recognizable for the user, so that the user can set up easily the region-of-interest within an optimal range.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
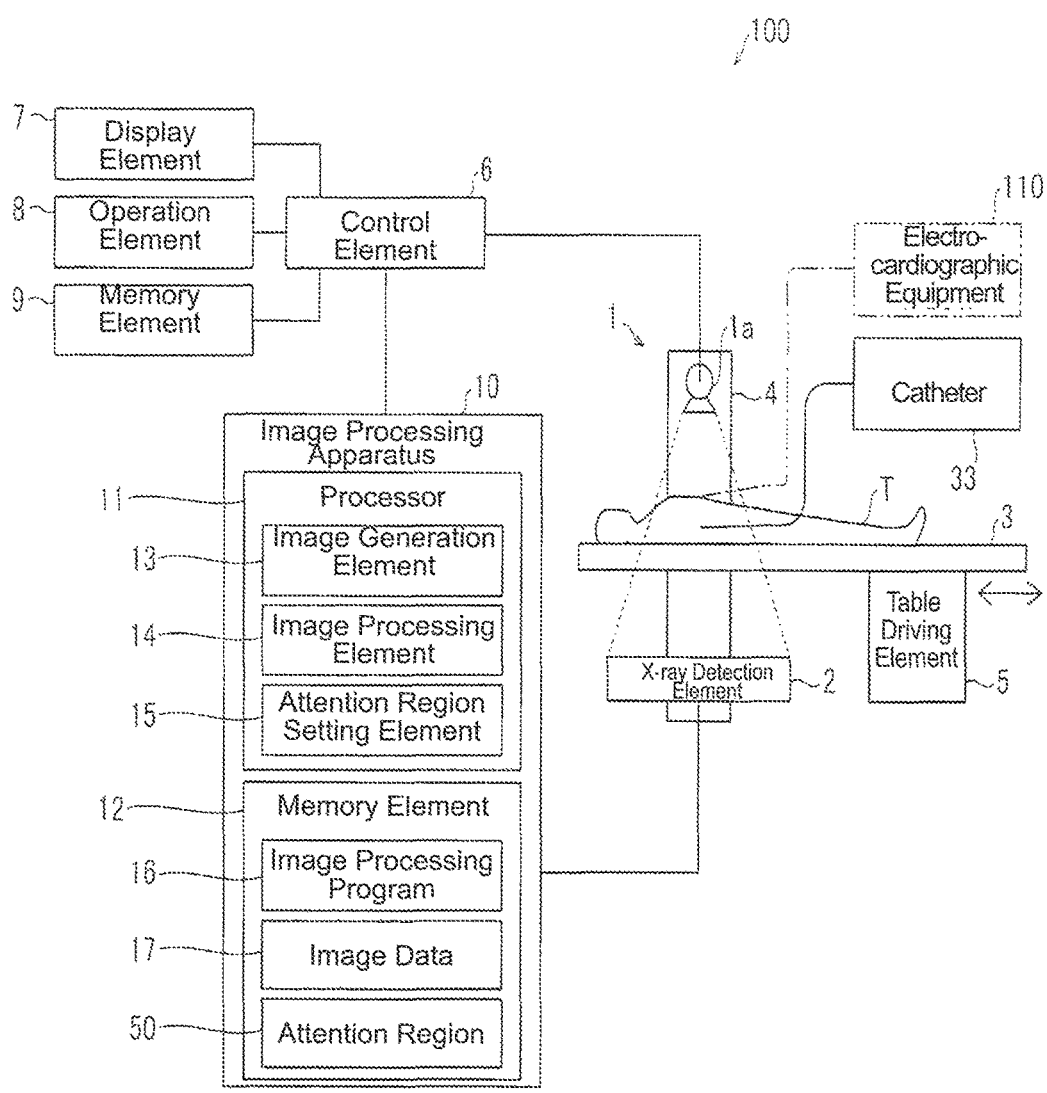
FIG. 1 is a block diagram illustrating an entire structure of an X-ray fluoroscopic imaging apparatus according to the aspect of the Embodiment 1 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, a computer-related system includes an input device for receiving data, an output device for outputting data in any tangible form (e.g. data transmission, image, memory recording, printing or displaying on a computer screen and all other forms), a memory for storing data as well as computer code, and a processor for executing stored computer code wherein said computer code resident in said memory will physically cause said processor to read-in data via said input device, process said data within said microprocessor and output said processed data via said output device.

It will be further understood by those of skill in the art that the apparatus and devices and the elements herein, without limitation, and including the sub components such as operational structures, elements, processors, and retained programs on and in circuits, communication pathways, and related wire and printed elements, control or driving elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer related process and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Preferred Aspect of the Embodiment

The inventor sets forth specific Embodiments of the present invention based on the following FIGs.

Embodiment 1

[System of an X-Ray Fluoroscopic Imaging Apparatus]

Referring to FIG. 1, the inventor illustrates the system of the X-ray fluoroscopic imaging apparatus 100 according to the aspect of the Embodiment 1 of the present invention.

The X-ray fluoroscopic imaging apparatus 100 according to the aspect of the Embodiment 1 is an apparatus that takes an X-ray image (fluoroscopic image) that is imaging the inside of the subject T by irradiating an X-ray from the outside of the subject T such as a human body and so forth.

The X-ray fluoroscopy imaging apparatus 100 comprises: an X-ray irradiation element 1, an X-ray detection element 2, a control element 6, a display element 7, an operation element 8, a memory element 9, and an image processing device 10.

The X-ray irradiation element 1 irradiates an X-ray toward a subject T. The detection element 2 detects the X-ray that transmits through the subject T. The X-ray irradiation element 1 and the X-ray detection element 2 are in-place facing to each other sandwiching a table 3 on which the subject T is loaded. The X-ray irradiation element 1 and the X-ray detection element 2 are supported by a moving mechanism 4 to be movable. The table 3 is horizontally movable by a table driving element 5. The moving mechanism 4 and the table driving element 5 are connected to the control element 6. The control element 6 moves the X-ray irradiation element 1, the X-ray detection element 2 and the table 3 by the moving mechanism 4 and the table driving element 5 so that the predetermined region of the subject T can be imaged as a fluoroscopic image 40 (refer to FIGS. 3A, 3B). A fluoroscopic image 40 that is the image of a target region of the subject T for an examination and a diagnosis that the user can arbitrarily set up.

The X-ray irradiation element 1 comprises an X-ray source 1a. The X-ray source 1a is an X-ray tube that is connected to a high-voltage source (not shown in FIG.) that emits an X-ray when high-voltages are added thereto. The X-ray source 1a is in place, in which an X-ray emission direction is facing the detection surface of the X-ray detection element 2. The X-ray irradiation element 1a is connected to the control element 6. The control element 6 controls the X-ray irradiation element 1 of which the X-ray source 1a emits X-ray in accordance with the preset imaging conditions including the tube voltage, an electric current and the time-interval between X-ray irradiations and so forth.

The X-ray detection element 2 that detects the X-ray that the X-ray irradiation element 1 irradiates and transmits the subject, and outputs a detection signal corresponding to the X-ray strength. The X-ray detection element 2 comprises e.g., a FPD (flat panel detector). The X-ray detection element 2 outputs the X-ray signal having a predetermined resolution to the image processing device 10. The image processing device 10 receives the X-ray detection signal from the X-ray detection element 2 and generates a fluoroscopic image 40 (refer to FIG. 3A, 3B).

The control element 6 is a computer comprising a CPU (central processing unit), ROM (read only memory) and RAM (random access memory) and so forth. The CPU executes the predetermined control program, so that the control element 6 is operative to control each unit of the X-ray fluoroscopic imaging apparatus 100. The control element 6 controls the X-ray irradiation element 1, the image processing device 10, and driving controls for the moving mechanism 4 and the table driving element 5.

The display element 7 is a monitor such as e.g., a liquid crystal display and so forth. The control element 6 controls the display element 7 to display the image that the image processing device 10 generates. The operation element 8 comprises, for example, a joy stick, a keyboard, a mouse, or other controller and so forth. The control element 6 receives the operation input through the operation element 8. The memory element 9 comprises a memory device such as e.g., a hard disk drive. The memory element 9 stores a variety of setting values including image data, an imaging condition and so forth. Each of the display element 7, the operation element 8 and the memory element 9 can be installed to the image processing device 10. In addition, the operation element 8 is an example of the input element in the claims.

The image processing device 10 enables to execute the image processing in real time while imaging the fluoroscopic image 40. The image processing device 10 is a computer comprising a processor 11 such as e.g., the CPU or a GPU (graphic processing unit), and the memory element 12 such as e.g., ROM and RAM. Specifically, the image processing device 10 executes the image processing program 16 stored in the memory element 12 by the processor 11. The image processing device can be made with the control element 6 in a unified manner by executing the image processing program with the same hardware (CPU) as the control element 6.

The memory element 12 stores the imaging processing program 16 that functions the computer as the image processing device 10. In addition, the memory element 12 stores the image data 17 including the fluoroscopic images 40 that the image generation element 13 generates, as set forth later, and the region-of-interest 50 that the region-of-interest setting element 15 sets up, as set forth later.

The image processing device 10 comprises: the image generation element 13 that is operative to execute the image processing program 16; the image processing element 14; and the region-of-interest setting element 15. Each of the image generation element 13, the image processing element 14, and the region-of-interest setting element 15 can be an individual and dedicated processor.

The image generation element 13 generates the fluoroscopic images 40 based on the detection signal of the X-ray that transmits the subject T. The image generation element 13 generates a video of the fluoroscopic images 40 based on the detection signals that the X-ray detection element 2 detects. Specifically, the X-ray irradiation element 1 intermittently irradiates the X-rays toward the subject T in a predetermined time-interval, and the X-ray detection element 2 detects such X-rays, in series, that transmit the subject T. The image generation element 13 images the detection signals, which the X-ray detection element 2 outputs in series, to generate the fluoroscopic image 40 by the predetermined frame rate. Such frame rate is e.g., approximately in the range of 15 FPS to 30 FPS. The fluoroscopic images 40 are the image having a pixel value of the predetermined gradation number (10-12 bits) in a grayscale. Accordingly, the brightness value of the pixel having a low pixel value is small to be displayed as black (dark), and the brightness value of the pixel having a large pixel value is large to be displayed as white (bright). In addition, the image can be inverted.

The image processing element 14 enables to execute an image processing (referring to FIGS. 4A-4C) that generates a superimposed image 41 by superimposing a plurality of the fluoroscopic images 40 that the image generation element 13 generates continuously. In addition, the image processing element 14 enables to execute an image processing (referring to FIGS. 5A-5C) that generates a stent-fixed image 43 in which the location of the stent 31 is fix-displayed based on the location data of the marker 34 in the fluoroscopic image 40. The image processing that the image processing device 14 executes is set forth later in detail. In addition, the stent 31 is an example of a device in the claim.

The user implements a surrounding operation an arbitrary region using the operation element 8 relative to the superimposed image 41 that the image processing element 14 image-processes, so that the region-of-interest setting element 15 can set up an arbitrary region as a region-of-interest 50. The inventor sets forth later the setting of the region-of-interest 50 using the region-of-interest setting element 15 in detail.

Figure 2:
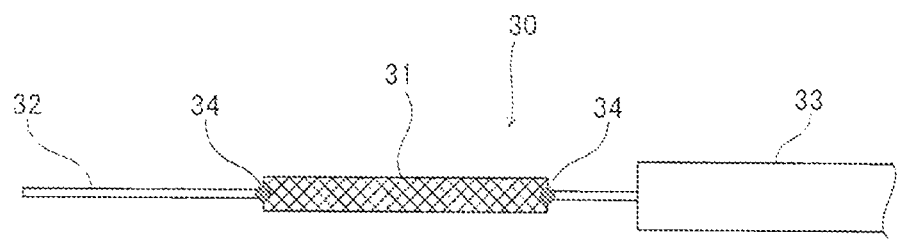
FIG. 2 is a schematic view illustrating one example of medical instruments including a stent.
Figure 3A:
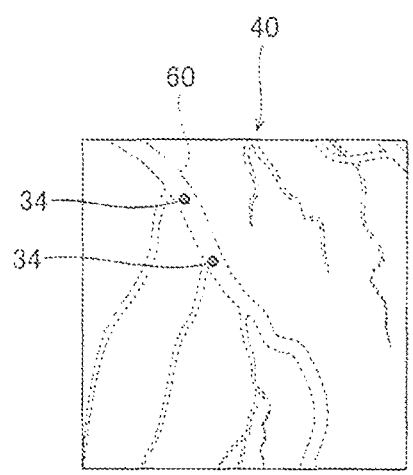
FIGS. 3A, 3B are schematic views illustrating one example of a fluoroscopic image.
Figure 3B:
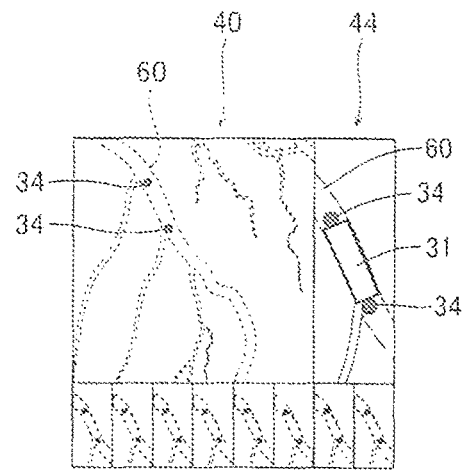

Referring to FIG. 2, according to the aspect of the Embodiment 1, the medical treatment instrument that is introduced inside the subject T includes a stent 31 for blood vessel medical treatment. The stent 31 is used, for example, to perform a coronary artery (cardiovascular) intervention treatment. The coronary artery intervention treatment is a medical treatment in which a catheter 33 having a guide wire 32 inside thereof is inserted into the blood vessel 60 of the subject T reaches to the coronary artery of the heart via the blood vessel 60. The stent 31 has a cylinder type web-structure made of such as a fine metal. The stent 31 is in place in the narrow region of the blood vessel 60 and dilated from inside thereof using a balloon to leave inside the blood vessel 60 so that the stent can dilate and support the blood vessel 60 from inside thereof. Referring to FIG. 3A, 3B, the stent 31 is hardly imaged into the fluoroscopic images 40 due to the web-structure thereof, so that the marker 34 made of a material through which the X-ray is less transmittable (or not transmittable) is installed to the stent 31 or the balloon as the marker. One or two markers 34 are installed thereto. In addition, the marker 34 is an example of the benchmark in the claims.

With regard to the coronary artery intervention treatment, the medical doctor introduces the catheter 33 into the coronary artery of the heart referring to the real-time video that is the fluoroscopic images 40 that the image processing device 10 continuously generates. With regard to the coronary artery intervention treatment, the blood vessel 60 and so forth move periodically due to the heartbeat, so that the real-time video is a continuous display of the X-ray images of which the imaging region moves periodically due to the heartbeat of the subject T. When such intervention is implemented, identification of the narrow region, positionings of the stent 31 and the balloon for blood vessel dilation to the narrow region, and confirmation following leaving the stent 31 are necessary. Accordingly, with regard to the coronary artery intervention treatment, the medical doctor must recognize accurately the location of the stent 31 while implementing a precise operation.

Figure 4A:
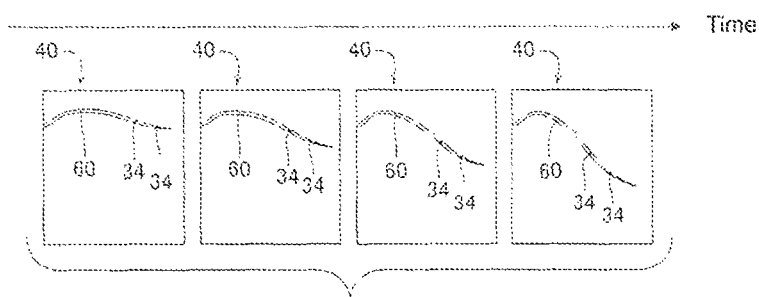
FIGS. 4A, 4B, 4C are schematic views illustrating setting up of the region-of-interest based on the movement range of the stent.
Figure 4B:
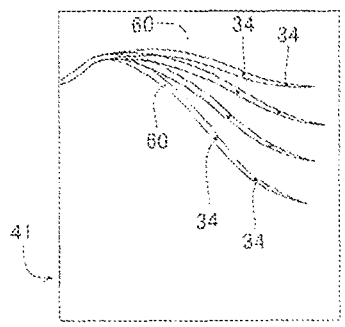
Figure 4C:
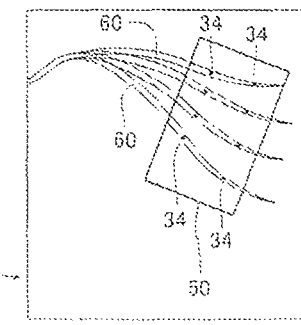

Now, relative to the X-ray fluoroscopic imaging apparatus according to the aspect of the Embodiment 1, referring to FIGS. 4A-4C, the image processing element 14 generates a superimposed image 41 by superimposing a plurality of the fluoroscopic images 40 that the image generation element 13 generates continuously. Now, the superimposed image 41 is used to facilitate to recognize the moving range of the stent 31. The region-of-interest setting element 15 sets up an arbitrary region, on which the user implements surrounding the arbitrary region using the operation element 8 relative to the superimposed image 41, as a region-of-interest 50. The image processing element 14 generates a stent-fixed image 43 in which the location of the marker 34 (i.e., stent 31) is fix-displayed based on the location data of the marker 34 in the region-of-interest 50 that the region-of-interest setting element 15 sets up. Followingly, the display element 7 displays the stent-fixed image 43, so that the user enables to recognize accurately the location of the stent 31 during the operation. In addition, the stent-fixed image 43 is an example of a device-fixed image in the claim.

(Superimposed Image)

The superimposed image 41 is the image that the display element 7 displays following superimposing the fluoroscopic images 40 that the image generation element 13 generates continuously. Specifically, referring to FIGS. 4A-4C, the image processing element 14 generates a superimposed image 41 by superimposing a plurality of the fluoroscopic images 40 that the image generation element 13 generates continuously. The control element 6 displays the superimposed image, which the image processing element 14 generates, on the display element 7. Along with updating the image data 17 of the fluoroscopic images 40 that are continuously generated, the superimposed image 41 that the display element 7 displays is also updated. In addition, referring to FIGS. 4A-4C, it is given that the superimposed image 41 is generated by superimposing four fluoroscopic images 40.

The movement locus of the marker 34 of the stent 31 that moves periodically due to heartbeat is displayed in the superimposed image 41. Accordingly, the user can easily recognize the movement range of the stent 31 by making sure the superimposed image 41 even when the stent is moving.

As set forth above, the display element 7 displays the fluoroscopic image 40 that the image generation element 13 generates based on the brightness value, so that the superimposed image 41 that the image processing element 14 generates by superimposing a plurality of the fluoroscopic images 40 that the image generation element 13 continuously generates is also displayed on the display element 7 based on the brightness value. Specifically, the image processing element 14 displays the movement locus on the display element 7 based on the brightness value relative to the fluoroscopic images 40. In such way, the location of the marker 34 is clearly displayed based on the difference of X-ray transmittance between the marker 34 made of the material having a small X-ray transmittance and the subject. As results, the user can easily make sure the location of the stent 31 relative to the fluoroscopic images 40.

The X-ray fluoroscopic imaging apparatus 100 according to the aspect of the Embodiment 1 sets up so that the number of the fluoroscopic images 40 that are superimposed to generate the superimposed image 41 is equivalent to the heartbeat. Referring to FIG. 1, an electrocardiographic equipment 110 is connected to the subject T and a number of the fluoroscopic images 40 that is equivalent to at least one per one heartbeat over time is superimposed to generate the superimposed image 41 based on the heartbeat measured using the electrocardiographic equipment 110. In addition, the superimposed image 41 is generated based on the heartbeat measured using the electrocardiographic equipment 110, so that the user can set up the number of fluoroscopic images 40 that are subject to superimposition.

(Setting of a Region-of-Interest)

The user sets up the desirable region-of-interest 50 by making sure the superimposed image 41 that the image processing element 14 generates. Specifically, as set forth above, the moving range of the stent 31 by the superimposed image 41, in which the movement locus of the marker 34 is denoted, is denoted so that the user can easily recognize even when the stent 31 moves. The user carries out the operation to specify the arbitrary four points (four location coordinates) to surround the movement locus while making sure the movement locus of the marker 34. The region-of-interest setting element 15 sets up the region-of-interest 50 in which the four points that the user specifies are the four corners. In such way, the user can accurately recognize the moving range of the stent 31 relative to the superimposed image 41, so that the user can set up the region-of-interest 50 including the entire moving range of the stent 31, which is the minimum range. In addition, the operation to set up the region-of-interest 50 is not limited to the method that selects the four arbitrary points and the operation by which the line is drawn is carried out to surround the movement locus.

According to the aspect of the Embodiment 1, as set forth above, the X-ray fluoroscopic imaging apparatus 100 generates a superimposed image 41 by superimposing the number of fluoroscopic images 40 that is equivalent to at least one per one-heartbeat, so that the movement locus of the marker 34 relative to the superimposed image 41 equals to at least one cycle of the stent 31 that periodically moves. In such case, the user can accurately recognize the movement range of the stent 31 relative to the superimposed image 41.

(Stent-Fixed Image 43)

The stent-fixed image 43 fix-displays the location of the stent 31, which is incorporated in the fluoroscopic images 40, in the image (display screen). The X-ray fluoroscopic imaging apparatus 100 according to the aspect of the Embodiment 1 generates the stent-fixed image 43 based on respective data of the partial fluoroscopic images 42 in which the region that is set up as the region-of-interest is cut off from the fluoroscopic images 40 that the image generation element 13 generates continuously.

Figure 5A:
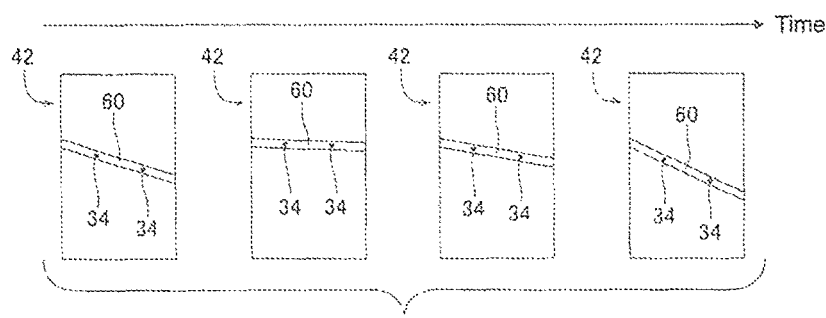
FIGS. 5A, 5B, 5C are schematic views illustrating a fix-display of the stent.
Figure 5B:
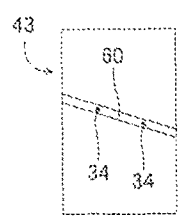
Figure 5C:
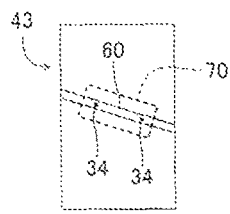

Specifically, referring to FIGS. 5A-5C, the image processing element 14 detects the marker 34 of the stent 31 from each of the partial fluoroscopic images 42. The detection of the marker can be achieved using a known image recognition technology. The image processing element 14 acquires the location coordinate data of the marker 34 in the partial fluoroscopic images 42 The image processing element 14 selects the base image that is a basis of the stent-fixed image 43 at the predetermined timing from a plurality of the partial fluoroscopic images 42 that is generated as a real-time video. The image processing element 14 aligns relative to the partial fluoroscopic images 42 of each frame following the base image so that the location of each marker 34 (stent 31) coincides with the location of the marker (stent 31) incorporated in the base image. Specifically, either horizontal move or rotative move or both moves are implemented relative to the partial fluoroscopic images 42 of each frame. Accordingly, the stent-fixed image 43, in which the locations of marker 34 (stent 31) coincides with each other, are generated every frame. As results, relative to the frames following the base image, the fluoroscopic images (stent-fixed images 43) are output continuously in the state in which the location of the marker 34 (stent 31) is fix-displayed.

The X-ray fluoroscopic imaging apparatus 100 according to the aspect of the Embodiment 1 generates the stent-fixed image 43 based on respective data of the partial fluoroscopic images 42 in which the region that is set up as the region-of-interest 50 is cut off, as set forth above. Specifically, the stent-fixed image 43 is generated based on the location data of the stent 31 relative to the region-of-interest 50 set up based on the data of the movement locus of the superimposed image 41 that the display element 7 displays. In such way, the stent 31 is located assuredly in the region-of-interest 50 and the stent-fixed image 43 can be generated, so that the detection accuracy of the stent 31 relative to the stent-fixed image 43 can be improved.

The stent-fixed image 43 that the image processing element 14 generates can be magnified and displayed. Specifically, the region 70 (referring to FIG. 5C) of the stent-fixed image 43 is cut off so that the entire marker 34 relative to the stent-fixed image 43 can be included, and referring to FIG. 3A, 3B, the region 70 is magnified and displayed as the magnified display image 44 adjacent to the fluoroscopic images 40.

(Effect According to the Aspect of the Embodiment 1)

The following effects can be obtained according to the aspect of the Embodiment 1.

According to the aspect of the Embodiment 1 as set forth above, the X-ray fluoroscopic imaging apparatus 100 comprises: the image generation element 13 that generates the fluoroscopic images 40 based on the detection signal of the radiation that transmits the subject T; the display element 7 that enables to display the fluoroscopic images 40; the image processing element 14 that executes an image processing to superimpose a plurality of fluoroscopic images 40 that the image generation element 13 generates continuously, and generates and displays the image denoting the movement locus of the marker 34 that denotes the location of the stent 31 introduced inside the body of the subject T; and the region-of-interest setting element 15 that set up the region-of-interest 50 including the movement locus relative to the superimposed image 41, in which the fluoroscopic images 40 are superimposed one another. In such way, the user can set up the region-of-interest 50 having a minimum range including the movement locus while confirming the movement locus of the marker 34 denoting the location of the stent 31 that the display element 7 displays. As results, even when the stent 31 introduced inside the body of the subject T moves, the movement range of the stent 31 is demonstrated to be easily recognizable for the user, so that the user can set up easily the region-of-interest 50 within an optimal range.

In addition, according to the aspect of the Embodiment 1, the movement locus 35 is the movement locus of the stent 31 that moves due to heartbeat of the subject T. When the location of the stent 31 must be recognizable accurately while the stent 31 inserted inside the blood vessel moves largely in accordance with the heartbeat, during such as the coronary intervention, the present invention is particularly effective in the case of which the movement range of the stent 31 is demonstrated to be easily recognizable for the user, so that the user can set up easily the region-of-interest 50 within an optimal range even when the stent 31 introduced inside the body of the subject moves.

In addition, according to the aspect of the Embodiment 1, the image processing element 14 displays the movement locus by superimposing the number of fluoroscopic images 40 that is equivalent to at least one per one heartbeat. Accordingly, at least one cycle of the movement locus 35 of the stent 31, of which the movement is periodically repeated by the heartbeat, can be displayed, so that the movement range of the stent 31 can be recognized more accurately.

According to the aspect of the Embodiment 1 and the Embodiment 2, the image processing element 14 enables to generate the stent-fixed image 43 that is processed to fix-display the location of the stent 31 based on the location data of the stent 31 in the region-of-interest 50 that is set up based on the data of the movement locus that the display element 7 displays, but the present invention is not limited thereto. In such way, the stent 31 is located assuredly in the region-of-interest 50 and the stent-fixed image 43 can be generated, so that the detection accuracy of the stent 31 relative to the stent-fixed image 43 can be improved. As results, the stent 31 can be assuredly fix-displayed.

In addition, according to the aspect of the Embodiment 1, the image processing element 14 displays the movement locus 35 on the display element 7 based on the brightness value relative to the fluoroscopic images 40. According to such aspect, the difference relative to the fluoroscopic images 40 between the stent 31 and the subject T can be clear by using the material having a low transmittance at least for a part of the stent 31, so that the location of the stent 31 as the marker 34 relative to the fluoroscopic images 40 can be clearly displayed. As results, the user can easily make sure the location of the stent 31 relative to the fluoroscopic images 40.

In addition, according to the aspect of the Embodiment 1, the X-ray imaging apparatus further comprises an input element 8 by which the user can input an input to set up the region-of-interest 50, and the region-of-interest setting element 15 sets up the region-of-interest 50 based on the data that the user inputs using the input element 8. According to such aspect, the user can set up the region-of-interest 50 within the range that the user desires.

Embodiment 2

Figure 6A:
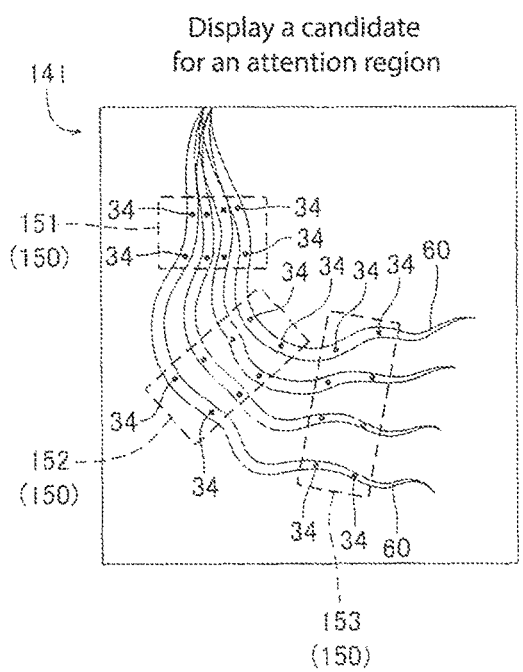
FIGS. 6A, 6B are schematic views illustrating setting up of the region-of-interest based on the movement range of the stent according to the aspect of the Embodiment 2.
Figure 6B:
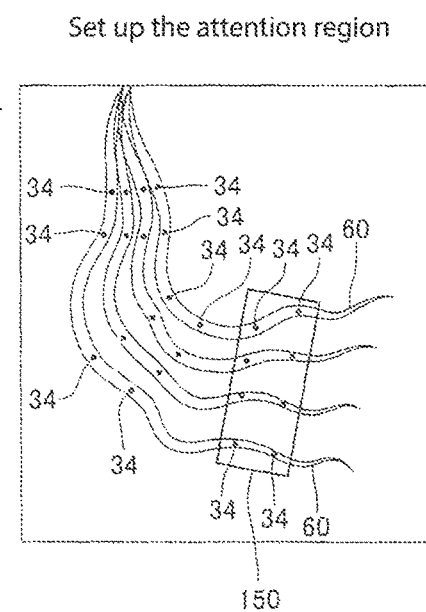

Next, referring to FIGS. 6A-6B, the inventor illustrates the aspect of the Embodiment 2. According to the aspect of the Embodiment 2, in addition to the Embodiment 1 set forth above, the inventor sets forth an example in which the region 151, 152, 153 that are candidates for the region-of-interest 50 can be selected and displayed. In addition, the same element as illustrated according to the aspect of the Embodiment 1 has the same sign in FIG.

According to the aspect of the Embodiment 2, when a plurality of the stent is displayed, each stent is displayed as a candidate of a region-of-interest relative to the fluoroscopic images 40 (referring to FIG. 3A, 3B) that the image generation element 13 continuously generates (referring to FIG. 1), and the user sets up the region-of-interest by selecting the arbitrary candidate.

Specifically, referring to FIG. 6A, 6B, when the three sets of the marker 34 corresponding to the three stents 31 are displayed relative to the superimposed image 41 that the image processing element 14 generates (referring to FIG. 1), the image processing element 14 displays the regions 151, 152, 153 as the candidate for each region-of-interest 150 so that the optimal range surrounds the movement locus of the marker 34 corresponding to each stent 31. Specifically, when the markers correspond to a plurality of the stents relative to the fluoroscopic images 40 (referring to FIG. 3A, 3B) that the image generation element 13 (referring to FIG. 1) generates, the display element 7 (referring to FIG. 1) displays the markers 34 corresponding to a plurality of the stents 31 even relative to the superimposed image 41 that the image generation element 13 generates continuously. The image processing element 14 displays the region 151, 152, 153 on the display element 7 so that the optimal range surrounds the movement locus based on the data of the movement locus of the marker 34 of the portion corresponding to each stent 31. The user selects the desired region among the regions 151, 152, 153 displayed on the display element 7. The region-of-interest setting element 15 (referring to FIG. 1) sets up such region, which is selected by the user, as the region-of-interest 150. In such way, the user can set up the region-of-interest 150 just by selecting the regions 151, 152, 153 displayed on the display element 7, so that the operation can be simpler than the case in which the user sets up the region-of-interest 150 by the operation that surrounds the marker 34 while making sure the superimposed image 41. Particularly, when a plurality of the stents 31 exists relative to the fluoroscopic images 40, the operation can become extremely simple. In addition, without limiting the marker 34 of the stent 31, the image processing element 14 may recognize a region, which resembles the stent 31 of the subject T, as the marker 34.

In other structural elements according to the aspect of the Embodiment 2 is the same as the aspect of the Embodiment 1 as set forth above.

(Effect According to the Aspect of the Embodiment 2)

According to the aspect of the Embodiment 2, as set forth above, the image processing element 14 selects and displays the region 151, 152, 153, which are candidates for the region-of-interest 150 based on the movement locus of the marker 34 denoting the location of the stent 31, on the display element 7. According to such aspect, the user can facilitate the operation compared to the case in which the user sets up the region-of-interest 150 by surrounding the region using the operation element 8 and so forth while making sure the movement locus displayed on the display element 7 so that the movement locus can be involved for setting up the region-of-interest 150. Particularly, when the user should watch a plurality of the targets, for example, when the device other than the target stent 31 exists in the fluoroscopic image 40, or when the region of the subject T that resembles the marker 134 of the stent 31, the operator can extremely simplify the operation to set up the region-of-interest 150. As results, the operator can further facilitate the operation to set up the region-of-interest 150.

Alternative Embodiment

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the aspect of the Embodiments 1 to the Embodiment 2 set forth above, the example of the X-ray fluoroscopic imaging apparatus 100 that is used for the intervention treatment of the coronary artery (cardiovascular blood vessel), but the present invention is not limited thereto. The present invention can be applied to an X-ray fluoroscopic imaging apparatus 100 that is used for other than the intervention treatment of the coronary artery (cardiovascular blood vessel). Even when the device introduced inside the body of the subject moves, the user can set up easily the region-of-interest within an optimal range by demonstrating the movement region of the device that is easily recognizable, so that the present invention is desirable also for the X-ray fluoroscopic imaging apparatus that is used for an interventional radiology treatment in the blood vessel. Even when the device introduced inside the body of the subject moves, the user can set up easily the region-of-interest within an optimal range by demonstrating the movement region of the device that is easily recognizable, so that the present invention is adequate in the case of which the fluoroscopic image of the region, in which the blood vessel moves in the image of the proximity of the heart, is taken care.

In addition, according to the aspect of the Embodiment 1 and the Embodiment 2, when the device introduced inside the body of the subject moves due to heartbeat, the example in which the movement range of the device is easily recognizable for the user is demonstrated, but the present invention is not limited thereto and e.g., can be applied to the case in which the device introduced inside the body of the subject moves due to the other factor such as an aspiration and so forth.

In addition, according to the aspect of the Embodiments 1 to 2 set forth above, the example of the device is the stent, but the present invention is not limited thereto. The present invention can be applied to any other device than the stent as long as that the device is introduced into the blood vessel.

In addition, according to the aspect of the Embodiment 2, when a plurality of the stents are included in the superimposed image, the image processing element displays the selectable candidate of the region-of-interest based on the movement locus of the marker of each stent, for example, but even when the superimposed image includes a plurality of the stents, according to the aspect of the Embodiment 1, the user can set up the region-of-interest by surrounding the movement locus of the marker while making sure the super imposed image.

According to the aspect of the Embodiment 1 and the Embodiment 2, the image processing element enables to generate the stent device-fixed image that is processed to fix-display the location of the stent based on the location data of the stent in the region-of-interest that is set up based on the data of the movement locus that the display element displays, but the present invention is not limited thereto. For example, the image processing element can just magnify and display the region-of-interest that is set up based on the data of the movement locus that the display element displays.

Those of skill would further appreciate that the various illustrative logical elements, blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

A processor may optionally also be implemented as a combination of computing devices including one or more processor units or elements, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

The computers described herein may be any kind of computer having at least one processor, either general purpose, or some specific purpose computer such as a workstation. The programs may be written in C, or Java, Brew or in any other programming language of any suitable kind known to those of skill in the art. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic imaging apparatus, comprising:
   an image generation element that generates a fluoroscopic image based on a detection signal of a radiation that transmits through a subject;
   a display element that enables a display of said fluoroscopic image and displays said fluoroscopic image;
   an image processing element that executes an image processing to superimpose a plurality of said fluoroscopic images that said image generation element continuously generates and generates an image denoting a movement locus of a benchmark denoting a location of a device introduced inside a body of said subject; and displays said image on said display element;
   a region-of-interest setting element that defines and displays a region-of-interest that includes said movement locus relative to a superimposed image of said fluoroscopic images;
   the region-of-interest being initially based on four user-specified location points that surround the movement locus; and
   said benchmark is detected in the region-of-interest after the region-of-interest is defined by the region-of-interest setting element.

2. The X-ray fluoroscopic imaging apparatus, according to the claim 1, wherein:
   said movement locus is a movement locus of said device that moves due to a heartbeat of said subject.

3. An X-ray fluoroscopic imaging apparatus, according to the claim 2, wherein:
   said image processing element superimposes a plurality number of said fluoroscopic images, said plurality number is equivalent to at least one per said heartbeat, and displays said movement locus.

4. The X-ray fluoroscopic imaging apparatus, according to the claim 1, wherein:
   said image processing element displays a candidate region for said region-of-interest on said display element in a selectable manner based on said movement locus.

5. The X-ray fluoroscopic imaging apparatus, according to the claim 1, wherein:
   said image processing element enables a generating of and generates a device-fixed image that said image processing element executes so that said display element fix-displays a location of said device based on location data of said device in said region-of-interest that said image processing element defined and displayed based on the data of said movement locus that said display element displays.

6. The X-ray fluoroscopic imaging apparatus, according to the claim 1, wherein:
   said image processing element displays said movement locus on said display element based on a brightness value of said fluoroscopic image.

7. The X-ray fluoroscopic imaging apparatus, according to the claim 1 further comprising:
   an input element that receives an input relative to a setup of said region-of-interest; wherein: said region-of-interest setting element defines and displays said region-of-interest based on the data that the user inputs.

8. The X-ray fluoroscopic imaging apparatus, according to the claim 1, wherein:
   said device is a stent that said user introduces inside a blood vessel.

* * * * *